(12) United States Patent
Nzike

(10) Patent No.: US 9,295,789 B2
(45) Date of Patent: Mar. 29, 2016

(54) RING CENTER NEEDLE

(75) Inventor: Philippe Nzike, Frankfurt am Main (DE)

(73) Assignee: Sanofi-Aventis Detuschland GmbH, Frankfurt am Main (DE)

( * ) Notice: Subject to any disclaimer, the term of this patent is extended or adjusted under 35 U.S.C. 154(b) by 0 days.

(21) Appl. No.: 14/115,813

(22) PCT Filed: May 4, 2012

(86) PCT No.: PCT/EP2012/058267
§ 371 (c)(1),
(2), (4) Date: Nov. 5, 2013

(87) PCT Pub. No.: WO2012/152705
PCT Pub. Date: Nov. 15, 2012

(65) Prior Publication Data
US 2014/0088514 A1    Mar. 27, 2014

(30) Foreign Application Priority Data
May 6, 2011    (EP) .................................... 11165130

(51) Int. Cl.
*A61M 5/00*    (2006.01)
*A61M 5/34*    (2006.01)
*A61M 5/31*    (2006.01)

(52) U.S. Cl.
CPC ............... *A61M 5/344* (2013.01); *A61M 5/345* (2013.01); *A61M 2005/3104* (2013.01); *A61M 2005/3125* (2013.01); *A61M 2005/3126* (2013.01); *A61M 2005/3128* (2013.01); *Y10T 29/49833* (2015.01)

(58) Field of Classification Search
CPC .............................. A61M 5/345; A61M 5/32
USPC .................................................. 604/171, 198
See application file for complete search history.

(56) References Cited

U.S. PATENT DOCUMENTS

| | | | |
|---|---|---|---|
| 3,134,380 A * | 5/1964 | Armao | ........................ 604/198 |
| 4,303,069 A | 12/1981 | Cohen | |
| 5,219,338 A | 6/1993 | Haworth | |
| 5,472,430 A | 12/1995 | Vaillancourt et al. | |
| 2003/0114797 A1 | 6/2003 | Vaillancourt et al. | |

FOREIGN PATENT DOCUMENTS

WO    9400172 A1    1/1994

\* cited by examiner

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

The present invention inter-alia relates to an apparatus comprising a needle guide configured to at last partially receive a needle of a needle assembly in a longitudinal opening and to center the needle of the needle assembly in the longitudinal opening, wherein the needle guide is longitudinally compressible.

19 Claims, 13 Drawing Sheets

RING CENTER NEEDLE

CROSS REFERENCE TO RELATED APPLICATIONS

The present application is a U.S. National Phase application pursuant to 35 U.S.C. §371 of International Application No. PCT/EP2012/058267 filed May 4, 2012, which claims priority to European Patent Application No. 11165130.3 filed May 6, 2011. The entire disclosure contents of these applications are herewith incorporated by reference into the present application.

FIELD OF INVENTION

The present patent application relates to medical devices of delivering at least two drug agents from separate reservoirs. Such drug agents may comprise a first and a second medicament. The medical device includes a dose setting mechanism for delivering the drug automatically or manually by the user.

BACKGROUND

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

SUMMARY

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with the primary reservoir and with a secondary reservoir of medicament containing at least one drug agent. The drug dispense interface can be a type of outlet that allows the two or more medicaments to exit the system and be delivered to the patient.

The combination of compounds as discrete units or as a mixed unit can be delivered to the body via a double-ended needle assembly. This would provide a combination drug injection system that, from a user's perspective, would be achieved in a manner that closely matches the currently available injection devices that use standard needle assemblies. One possible delivery procedure may involve the following steps:

1. Attach/mount a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach/mount a dose dispenser, such as a double-ended needle assembly, to a connecting part at the distal end of the dispense interface. In this manner, a proximal end of the needle assembly is in fluidic communication with both the primary compound and secondary compound. For instance, a needle hub of the needle assembly is screwed on the connecting part of the dispense interface and thereby one end of a needle of the double-ended assembly intrudes into an outlet of the connecting part of the dispense interface, pierces a septum of the dispense interface arranged at the outlet and resides in fluid communication with a holding chamber of the dispense interface. The holding chamber may be in fluid communication with the first and second proximal needle.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable.

5. Optionally, after the second dose has been computed, the device may be placed in an armed condition. In such an optional armed condition, this may be achieved by pressing and/or holding an "OK" button on a control panel. This condition may provide for greater than a predefined period of time before the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

After a specific number of injections (e.g. 1 injection, 3 injections, 5 injections, 10 injections, 20 injections, 50 injections or the like) there is a risk for the dose dispenser and/or the dispense interface to be contaminated and, additionally, the tips of the needles of the dose dispenser and/or the dispense interface may be blunted. For instance, a blunted tip of a needle may not be able to sufficiently pierce a septum and/or tissue, for instance inserting a blunted needle in a desired injection site may be very painful. Furthermore, mechanical parts of the dose dispenser and/or the dispense interface such as a valve arrangement may only proper function for a specific number of injections (e.g. 1 injection, 3 injections, 5 injections, 10 injections, 20 injections, 50 injections or the like).

Therefore, the dose dispenser and the dispense interface are disposable parts. For instance, the dose dispenser should only be used for one injection and the dispense interface should only be used with one first and second reservoir. However, attaching the dose dispenser to the connecting part of the dispense interface may be fiddly, for instance the diameter of the outlet may be about the diameter of the needle. Furthermore, the double-ended needle can jam (e.g. tilt) and, for instance, collide with side-walls of the holding chamber and damage the dispense interface. For instance, the needle assembly and, in particular, the double-ended needle may initially tilt when screwing the needle assembly on a connecting part of the dispense interface (e.g. because of the helix angle of the thread).

To facilitate attaching the dose dispenser to the connecting part of the dispense interface and to prevent a collision of the double-ended needle with side-walls of the holding chamber a cross-sectional inner diameter of the outlet and the holding-chamber and/or a length of the holding chamber and/or a length of the double-ended needle may be increased and, correspondingly, the volume of the holding chamber and/or the liquid path is also increased.

However, it is desired to minimize the liquid dead volume and the liquid path in front of the first and second reservoir, for instance the volume of the fluid communication paths in the dispense interface. For instance, there is a higher risk that a medicament contained in this liquid dead volume may be contaminated and/or cause any other undesired side-effects These side-effects may be for instance due to a lowered stability, compromised therapeutic performance and toxicology of a combination of the first and second medicament.

Therefore, the present invention inter-alia faces the technical problem of facilitating attaching a dose dispenser to a connecting part such as a connecting part of a dispense interface and/or a medical device such as a drug delivery device and/or to minimize the liquid dead volume thereof. However, the present invention is not limited to a connecting part of a dispense interface and/or a medical device as described above and may basically relate to a connecting part of any dispenser such as a dispenser configured to eject adhesives such as multi-component adhesives (e.g. two-component adhesives) or the like.

According to the present invention, an apparatus comprises a needle guide configured to at last partially receive a needle of a needle assembly in a longitudinal opening and to center the needle of the needle assembly in the longitudinal opening, wherein the needle guide is longitudinally compressible.

Furthermore according to the present invention, a method comprises receiving, at an apparatus, a needle of a needle assembly in a longitudinal opening of a needle guide, and centering the needle of the needle assembly in the longitudinal opening, wherein the needle guide is longitudinally compressible.

The apparatus may be a dispenser. In particular, the apparatus may be a drug delivery device such as a medical device configured to eject a drug agent (e.g. a dose of a medicament) such as an infusion device or an injection device, for instance an insulin injection pen. Injection devices may be used either by medical personnel or by patients themselves. As an example, type-1 and type-2 diabetes may be treated by patients themselves by injection of insulin doses, for example once or several times per day.

For instance, the apparatus is a medical device configured to eject at least two drug agents from separate reservoirs comprising a first and a second medicament, respectively, but it is not limited thereto. Alternatively, the medical device is for instance a conventional medical device configured to eject a drug agent from a single reservoir such as Applicant's Solostar insulin injection pen.

Alternatively, the apparatus may be a disposable part attachable to a dispenser such as a drug delivery device such as a medical device configured to eject a medicament. For instance, the apparatus is a dispense interface attachable to a medical device configured to eject a drug agent. A dispense interface may be configured to be in fluid communication with at least one reservoir of the medical device containing at least one medicament. For instance, the drug dispense interface is a type of outlet that allows the at least one medicament to exit the medical device. The dispense interface may comprise a valve arrangement. Such a valve arrangement may be configured to prevent contamination of the at least one medicament in the at least one reservoir. For instance, the valve arrangement is configured to prevent back flow of the at least one medicament when the medicament is delivered/ejected.

Alternatively, the apparatus may be the needle guide. The needle guide may be (reversibly and/or irreversibly) attachable to a connecting part such as a connecting part of a dispense interface and/or a dispenser such as a drug delivery device.

The needle-assembly may be a dose dispenser. For instance, the needle assembly is configured to be in fluid communication with a holding chamber of a dispense interface and/or at least one reservoir of a dispenser such as a drug delivery device. The reservoir may contain at least one fluid such as a medicament.

For instance, the needle assembly is a double-ended needle assembly and/or a standard needle assembly. The needle assembly may comprise a needle, a needle hub and a removable protecting cover. The needle may be a double-ended needle. One end of the double ended needle may be configured to be inserted into a desired injection site before an injection. The other end of the double ended needle may be configured to pierce a septum of a connecting part such as a connecting part of a dispense interface and/or a drug delivery device as described above. The needle hub may be configured to attach the needle assembly to the connecting part such as a connecting part of the dispense interface and/or the dispenser such as the drug delivery device. For instance, the needle hub comprises an internal thread corresponding to an outer thread of the connecting part.

According to the present invention, the needle guide is configured to receive a needle of the needle assembly in a longitudinal opening and to center the needle in the longitudinal opening. The needle may be considered to be centered in the longitudinal opening of the needle guide, when the longitudinal axis of the longitudinal opening and the longitudinal axis of the needle are equal, i.e. the needle and the longitudinal opening are coaxial. In particular, the needle may be considered to be centered in the longitudinal opening of the needle guide, when one end of the needle being in the longitudinal opening is in the center of a cross section of the longitudinal opening.

For instance, when the needle assembly is received in the longitudinal opening, the needle assembly may be laterally secured in the longitudinal opening. For instance, a rim of the longitudinal opening is configured to engage with a corresponding recess of the needle assembly such that, when the rim of the longitudinal opening is in engagement with the corresponding recess of the needle assembly, the needle is centered in the longitudinal opening. Alternatively or additionally, the longitudinal opening may have a (circular) setback configured to receive a rim of the needle assembly such that, when the rim of the needle resides on the setback of the longitudinal opening, the needle is centered in the longitudinal opening.

Furthermore, according to the present invention, the needle guide is longitudinally compressible. In particular, the longitudinal opening of the needle guide may be longitudinally compressible. For instance, when a force is applied on the longitudinal opening of the needle guide in direction of the longitudinal axis of the longitudinal opening, the longitudinal length of the longitudinal opening of the needle guide is reduced.

As an example, the needle guide is arranged at a connecting part of a dispense interface such that the longitudinal opening at least partially encompasses the connecting part of the dispense interface and an outlet of the connecting part is in the center of a cross section of the longitudinal opening. In this example, when a needle assembly is received in the longitudinal opening, one end of a needle of the needle assembly may be spaced from and centered on the outlet of the connecting part. The outlet of the connecting part may be an opening at the center of the connecting part and is configured to receive one end of a needle of the needle assembly. If the needle assembly is pushed in direction of the longitudinal axis of the longitudinal opening in order to attach the needle hub of the needle assembly to the connecting part of the dispense interface as described above, the needle assembly may be laterally secured in the longitudinal opening and the one end of the needle may straightly approach the outlet along the longitudinal axis of the longitudinal opening.

For instance, the smallest diameter of the longitudinal opening (or of the longitudinally compressible portion thereof) may be at least a third, preferably at least a half, more preferably at least once or twice of the longitudinal length of the longitudinal opening. This is inter-alia advantageous to stablilize the needle guide, when the longitudinal opening is longitudinally compressed, and/or to allow the needle to straightly approach the outlet and/or to prevent a tilting of the needle, when the longitudinal opening is longitudinally compressed.

For instance, the needle hub of the needle assembly is screwed on the connecting part of the dispense interface and thereby one end of a needle of the double-ended assembly straightly intrudes into the outlet of the connecting part of the dispense interface, pierces a septum of the dispense interface arranged at the outlet and resides in fluid communication with a holding chamber of the dispense interface. Therein, the needle guide centers the needle and prevents a tilting of the needle. In other words, the needle guide may preferably be configured to hold the needle in the center of the longitudinal opening, when the needle guide is longitudinally compressed, such that the needle guide allows the needle to straightly approach the outlet and/or to prevent a tilting of the needle.

Accordingly, the risk of a collision of the needle with side-walls of the holding chamber and/or the outlet is significantly reduced, such that the cross-sectional inner diameter of the holding-chamber and/or the outlet may correspond to the outer diameter of the needle, for instance the inner diameter of the holding-chamber and/or the outlet is only slightly larger (e.g. 5%, 10% or 25% larger) than the outer diameter of the needle. Alternatively or additionally, the length of the needle and/or the holding chamber can accordingly be decreased such that the one end of the needle of the needle assembly may be completely inside the needle hub and may intrude into the outlet after the needle hub touches the connecting part.

The present invention is inter-alia advantageous in order to facilitate attaching a dose dispenser to a connecting part such as a connecting part of a dispense interface and/or a dispenser such as a drug delivery device. Furthermore, the present invention is inter-alia advantageous in order to minimize the liquid dead volume in a dispense interface and/or in front of a reservoir of a dispenser such as a drug delivery device.

In the following, features and embodiments (exhibiting further features) of the present invention will be described, which are understood to equally apply to the apparatus and the method as described above. These single features/embodiments are considered to be exemplary and non-limiting, and to be respectively combinable independently from other disclosed features/embodiments of the apparatus and the method as described above. Nevertheless, these features/embodiments shall also be considered to be disclosed in all possible combinations with each other and with the apparatus and the method as described above. For instance, a mentioning that an apparatus according to the present invention is configured to perform a certain action should be understood to also disclose an according method step of the method according to the present invention.

According to an embodiment of the present invention, the longitudinal opening has a circular cross-section and/or is cylindrical. Alternatively or additionally, the cross-section of the longitudinal opening may be elliptical and/or round. The longitudinal opening may be a cylinder having a longitudinal opening (e.g. a through opening).

For instance, standard needle assemblies typically also have a circular cross-section. For instance, an inner diameter of the longitudinal opening may be adapted to an outer diameter of a standard needle assembly. In particular, the inner diameter at a rim of the longitudinal opening may be adapted to an outer diameter of a rim of the standard needle assembly. This embodiment is inter-alia advantageous to enable receiving a standard needle assembly in the longitudinal opening.

According to an embodiment of the present invention, the longitudinal opening is defined by a longitudinally compressible lateral surface. As described above, when a force is for instance applied on the longitudinal opening of the needle guide in direction of the longitudinal axis of the longitudinal opening, the longitudinal length of the lateral surface defining the longitudinal opening of the needle guide is reduced. This embodiment is inter-alia advantageous in order to allow a longitudinal compression of the longitudinal opening.

According to an embodiment of the present invention, the lateral surface is foldable. As an example, the lateral surface is (only) foldable in direction of the longitudinal axis of the longitudinal opening such that (only or mainly) the longitudinal stiffness of the lateral surface is decreased. In this example, when a needle assembly is received in the longitudinal opening and is pushed at an angle in direction of the longitudinal axis of the longitudinal opening, the lateral stiffness of the lateral surface may at least partially prevent a tilting/jamming of the needle.

This embodiment is inter-alia advantageous in order to define a preferred direction for the compression of the longitudinal opening and/or to prevent a jamming/tilting of the needle of the needle assembly.

According to an embodiment of the present invention, the foldable lateral surface is formed like bellows. The cross-section of the bellows like lateral surface may be "V-shaped". For instance, the lateral surface has the property of bending and ceasing. Alternatively or additionally, the foldable lateral surface is wavelike. As described above, this embodiment is inter-alia advantageous in order to define a preferred direction for the compression and/or to prevent a jamming/tilting of the needle of the needle assembly.

According to an embodiment of the present invention, the lateral surface is made from an elastic material.

For instance, the needle guide is made from elastic plastics such as injection moldable elastic plastics.

The elasticity of the material may cause an elastic counterforce, when the longitudinal opening and/or the lateral surface thereof is compressed. For instance, the compressed longitudinal opening, like a compressed spring washer, secures a screw connection between a needle hub of the needle assembly and a connecting part of a dispense interface and/or a dispenser such as a drug delivery device.

Furthermore, the elasticity of the material may also cause an elastic counterforce, when a needle assembly is received in the longitudinal opening and is pushed at an angle in direction of the longitudinal axis of the longitudinal opening.

This embodiment is inter-alia advantageous to secure a connection between a needle hub of the needle assembly and a connecting part and/or to prevent a jamming/tilting of the needle.

According to an embodiment of the present invention, the lateral surface has at least one longitudinal slit. The slit may allow to reversibly spread (i.e. enlarge) the longitudinal opening. This embodiment is inter-alia advantageous to reversibly attach the needle guide to a connecting part of a dispense interface and/or a dispenser such as a drug delivery device and/or to receive the needle assembly in the longitudinal opening.

According to an embodiment of the present invention, the longitudinal opening has a circular set-back configured to receive a rim of the needle assembly. The set-back may be arranged in a plane perpendicular to the longitudinal axis of the longitudinal opening. For instance, the lateral surface of the longitudinal opening has a circular set-back such that the inner diameter of the longitudinal opening is enlarged at the set-back. For instance, the enlarged inner diameter may correspond to the outer diameter of the rim of the needle assembly. For instance, the set-back and/or the longitudinal opening is configured to form a lateral form fit with the needle assembly. The needle assembly may be a standard needle assembly. As described above, this embodiment is inter-alia advantageous to center the needle of the needle assembly and to secure the needle assembly laterally.

Alternatively or additionally, the longitudinal opening may have a circular notch configured to receive a rim of the needle assembly. In this case, the diameter of the longitudinal opening may be spreadable to allow receiving the rim of the needle assembly in the circular notch. The needle assembly may be (laterally and longitudinally) secured in the longitudinal opening. For instance, the notch and/or the longitudinal opening is configured to form a longitudinal and lateral form fit with the needle assembly. This embodiment is inter-alia advantageous to attach the needle assembly to the needle guide prior to attaching the needle guide to a connecting part of dispenser interface and/or a dispenser such as a drug delivery device or the like.

According to an embodiment of the present invention, the needle guide is configured to encompass a connecting part of a medical device configured to eject a medicament. The medical device may be a drug delivery device as described above.

As described above, the longitudinal opening may be configured to at least partially encompass the connecting part of the medical device such that an outlet of the connecting part is in the center of a cross section of the longitudinal opening.

The longitudinal opening may be a through opening. For instance, the longitudinal opening is configured to at least partially receive at one end the connecting part of the medical device and at the other end the needle assembly. This embodiment is inter-alia advantageous to allow a reversible or irreversible attachment of the needle guide to the connecting part of the medical device.

Alternatively, as described above, the longitudinal opening may at least partially encompass the connecting part of the medical device such that an outlet of the connecting part is in the center of a cross section of the longitudinal opening. For instance, the needle guide is irreversibly attached to the connecting part of the medical device and/or the needle guide and the connecting part of the medical device are integrally formed.

According to an embodiment of the present invention, the apparatus is attachable to the medical device. In particular, the needle guide is (reversibly or irreversibly) attachable to the medical device. For instance, the medical device and the needle guide comprise mating attachment means configured to form a frictional fit, a form fit and/or an interference fit. Examples of mating attachment means include snap locks, snap fits, snap rings, keyed slots, threads and any combinations thereof. Examples of mating attachment means include snap locks, snap fits, snap rings, keyed slots, threads and any combinations thereof. Alternatively or additionally, the apparatus may be configured to be glued to the medical device.

When the needle guide is attached to the medical device, the longitudinal opening may at least partially encompass a connecting part of the medical device and an outlet of the connecting part may be in the center of a cross section of the longitudinal opening. The medical device may be a drug delivery device as described above.

This embodiment is inter-alia advantageous to allow an attachment of the needle guide to the connecting part of the medical device.

According to an embodiment of the present invention, the apparatus is a medical device configured to eject a medicament, wherein the needle guide encompasses a connecting part of the medical device. The medical device may be a drug delivery device as described above. The longitudinal opening may at least partially encompass the connecting part of the medical device such that an outlet of the connecting part is in the center of a cross section of the longitudinal opening.

According to an embodiment of the present invention, a needle hub of the needle assembly is configured to be attached to the connecting part of the medical device. In particular, the needle assembly may be configured to be reversibly attached to the connecting part of the medical device. The needle hub and the connecting part may comprise mating attachment means configured to form a frictional fit, a form fit and/or an interference fit. Examples of mating attachment means include snap locks, snap fits, snap rings, keyed slots, threads and any combinations thereof. For instance, the needle hub comprises an internal thread corresponding to an outer thread of the connecting part.

This embodiment is inter-alia advantageous to allow a reversible attachment of the needle assembly to the connecting part of the medical device.

According to an embodiment of the present invention, one end of a needle of the needle assembly is configured to intrude into an outlet of the connecting part and to pierce a septum of the medical device. For instance, a needle hub of the needle assembly is screwed on the connecting part of the dispense interface and/or the medical device and thereby one end of a needle of the double-ended assembly intrudes into an outlet of the connecting part of the dispense interface, pierces a septum arranged at the outlet and resides in fluid communication with a holding chamber of the dispense interface and/or a reservoir of the medical device.

According to an embodiment of the present invention, the method comprises longitudinally compressing the needle guide, attaching the needle assembly to a connecting part of the medical device, intruding the needle of the needle assembly into an outlet of the needle hub, and piercing a septum of the medical device.

BRIEF DESCRIPTION OF THE DRAWINGS

These as well as other advantages of various aspects of the present invention will become apparent to those of ordinary skill in the art by reading the following detailed description, with appropriate reference to the accompanying drawings, in which.

DETAILED DESCRIPTION

Figure 1:
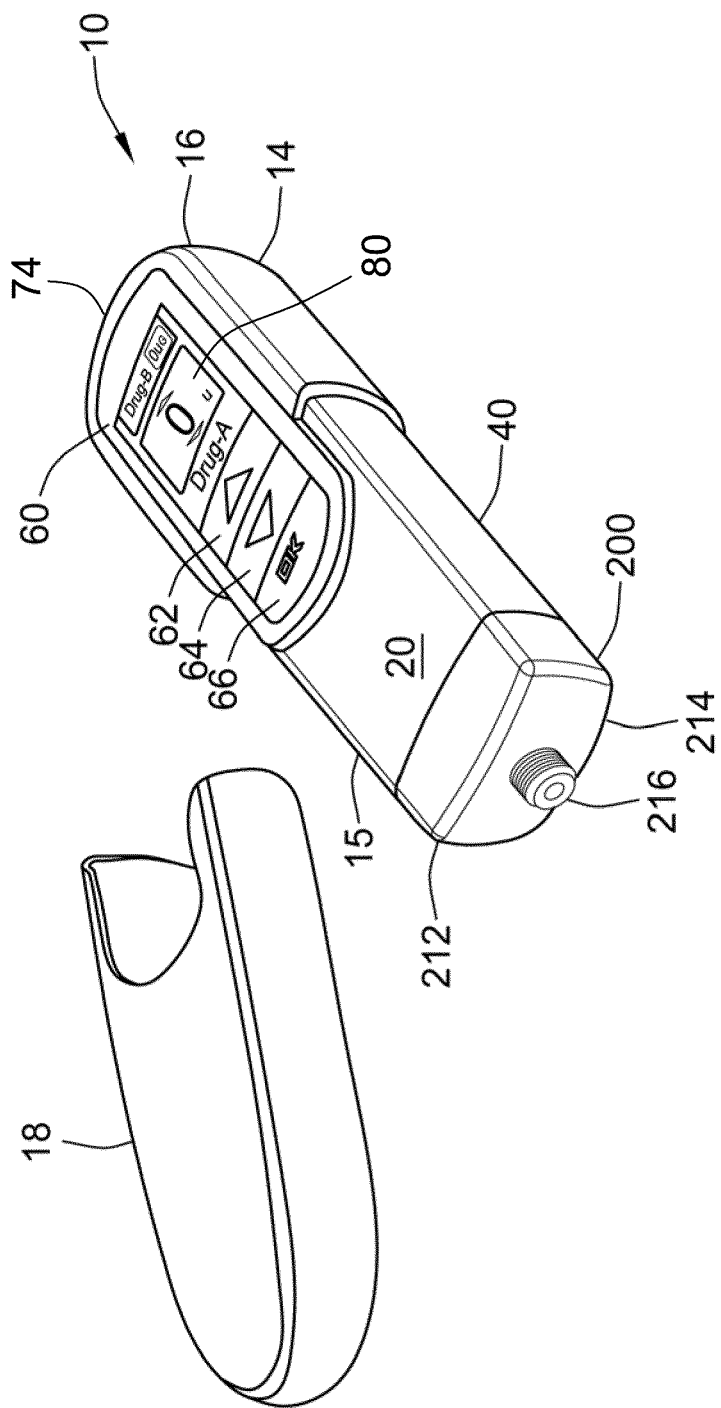
FIG. 1 illustrates a perspective view of the delivery device illustrated in FIGS. 1a and 1b with an end cap of the device removed.
Figure 2:
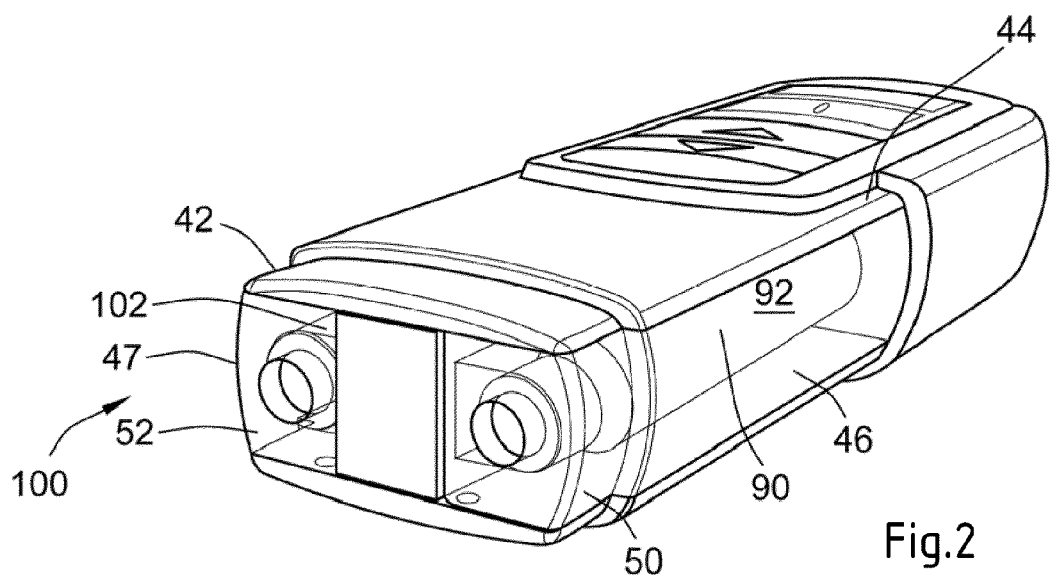
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a connecting part such as needle hub 216. This needle hub 216 may be configured so as to allow a dose dispenser, such as a conventional pen type injection needle assembly, to be removably mounted to the drug delivery device 10. The needle hub 216 has an outer diameter 217 at the end 219.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
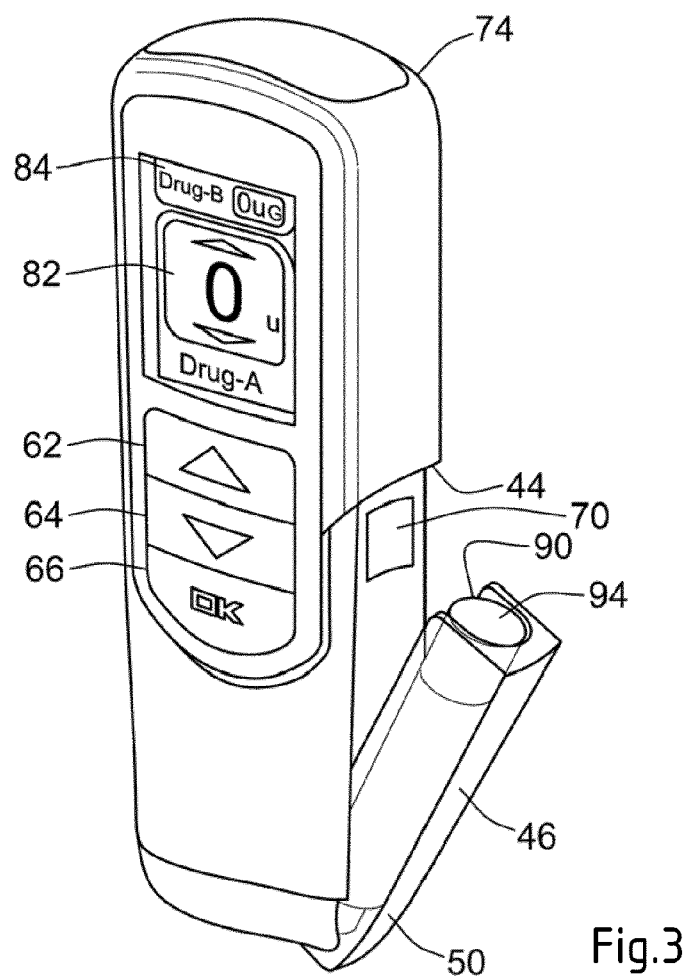
FIG. 3 illustrates a perspective view of the cartridge holder illustrated in FIG. 1 with one cartridge retainer in an open position.

As shown in FIG. 3, the first and a second cartridge retainers 50, 52 comprise hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
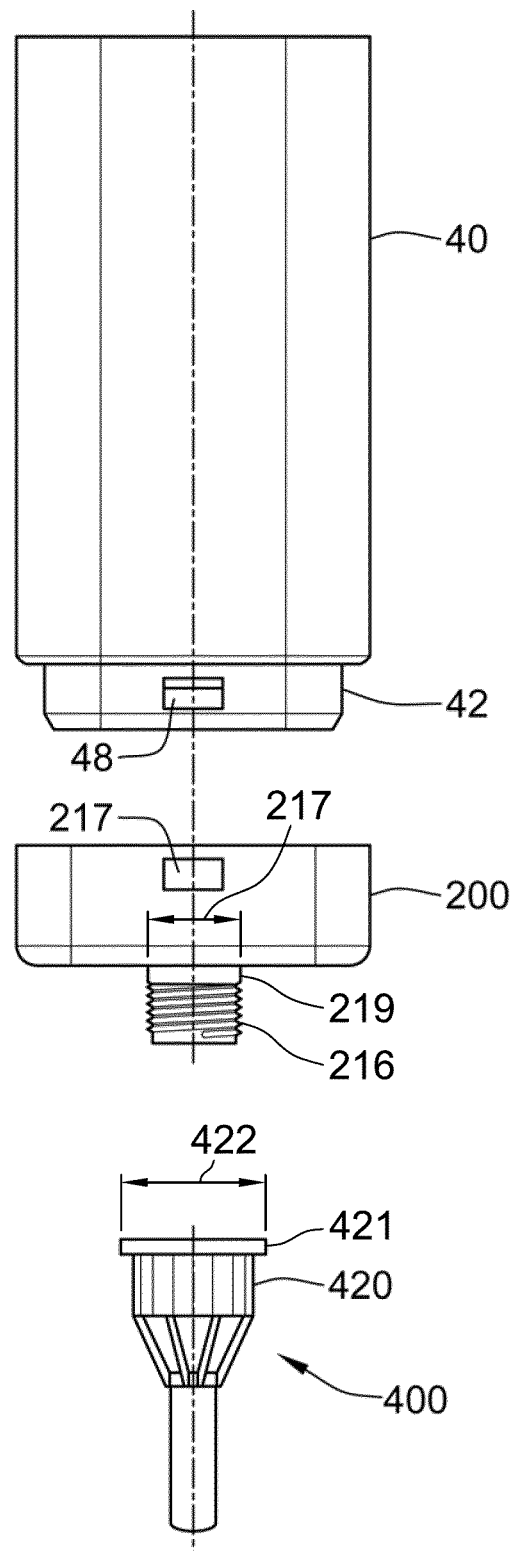
FIG. 4 illustrates a dispense interface and a dose dispenser that may be removably attached on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420. The protective cover 420 has a rim 421 and an outer diameter 422 at the rim 421.

Figure 5:
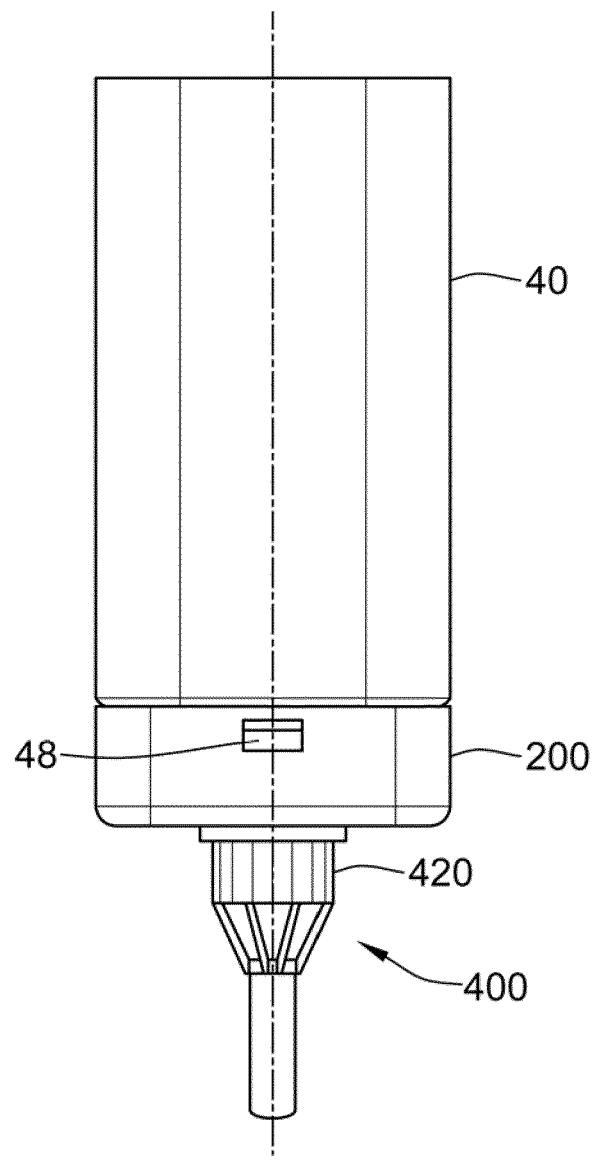
FIG. 5 illustrates the dispense interface and the dose dispenser illustrated in FIG. 4 attached on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
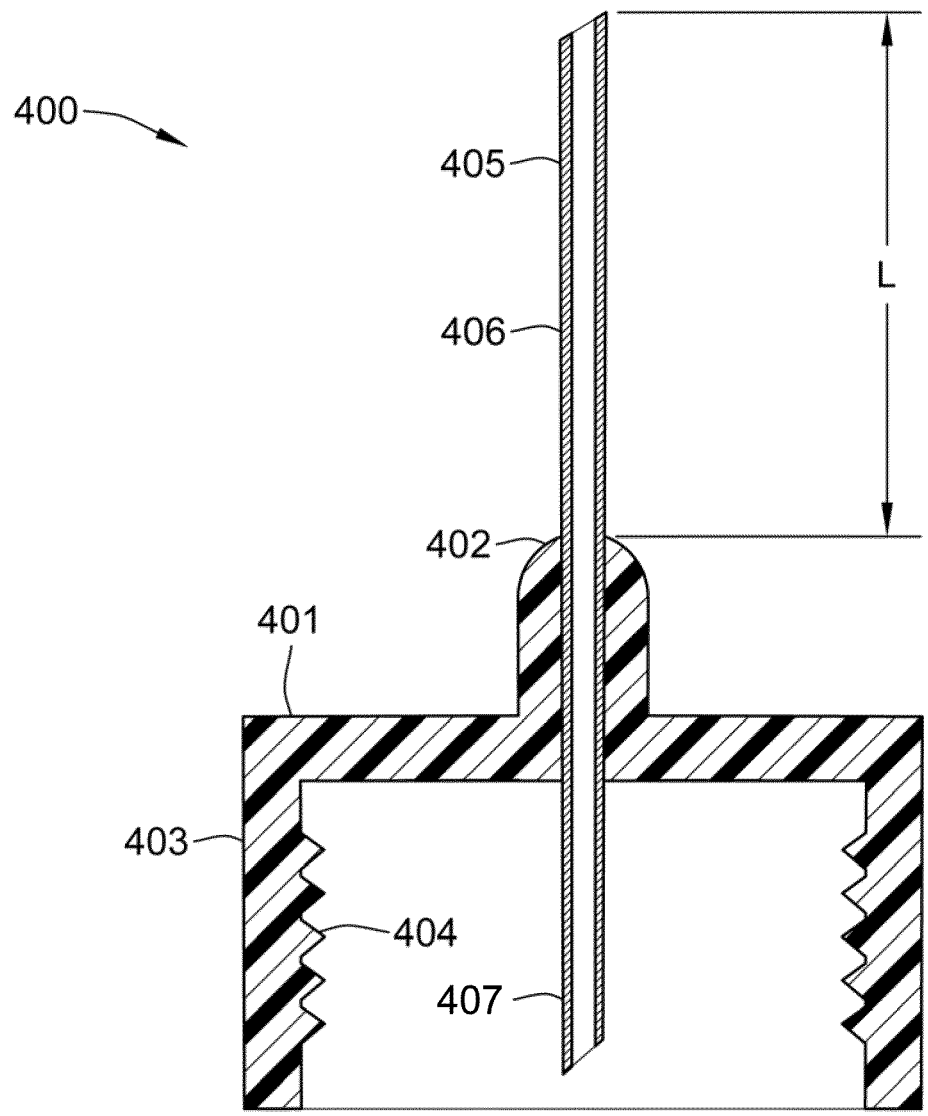
FIG. 6 illustrates one arrangement of the dose dispenser that may be mounted on a distal end of the delivery device.
Figure 7:
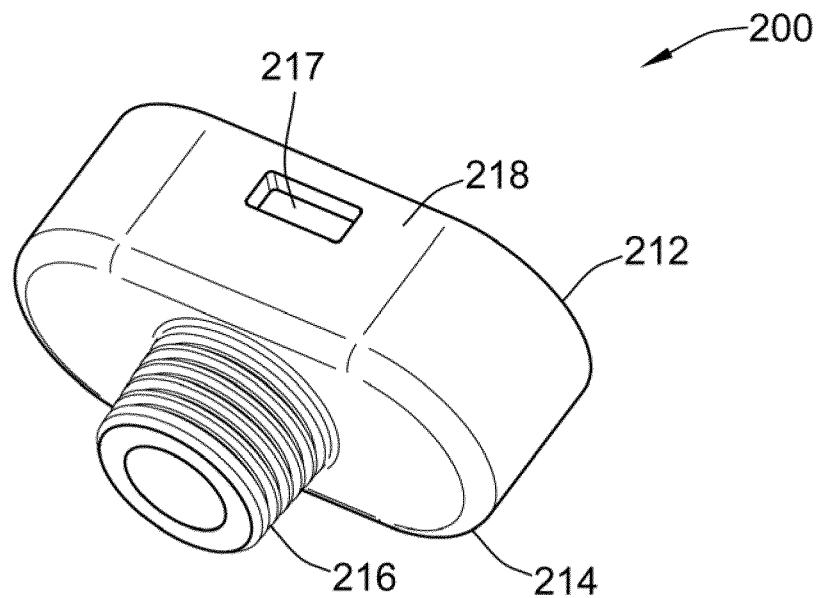
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the needle hub 216 of dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 407 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:
  a. a main outer body 210,
  b. an first inner body 220,
  c. a second inner body 230,
  d. a first piercing needle 240,
  e. a second piercing needle 250,
  f. a valve seal 260, and
  g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10.

For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
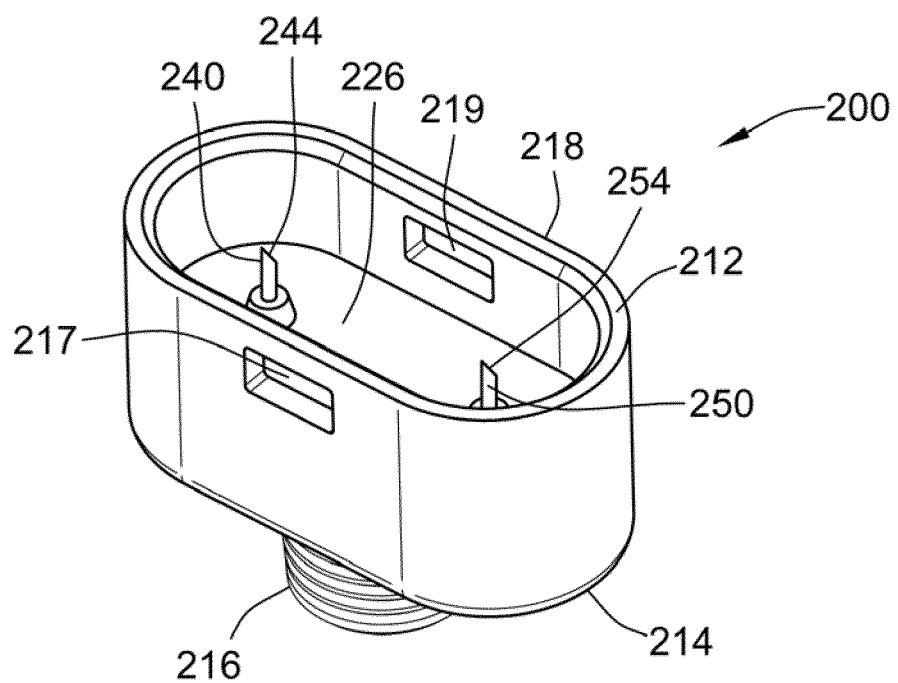
FIG. 8 illustrates another perspective view of the dispense interface illustrated in FIG. 4.
Figure 9:
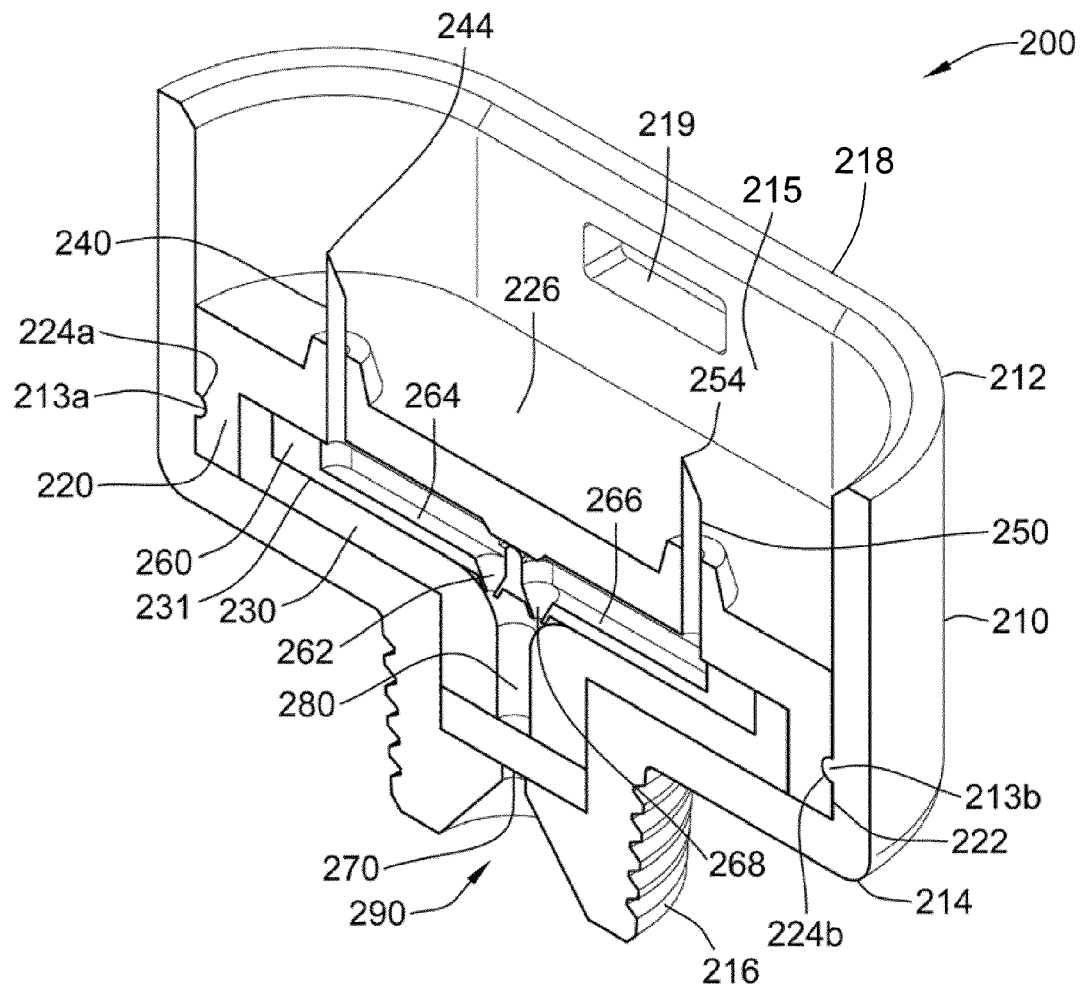
FIG. 9 illustrates a cross-sectional view of the dispense interface illustrated in FIG. 4.
Figure 10:
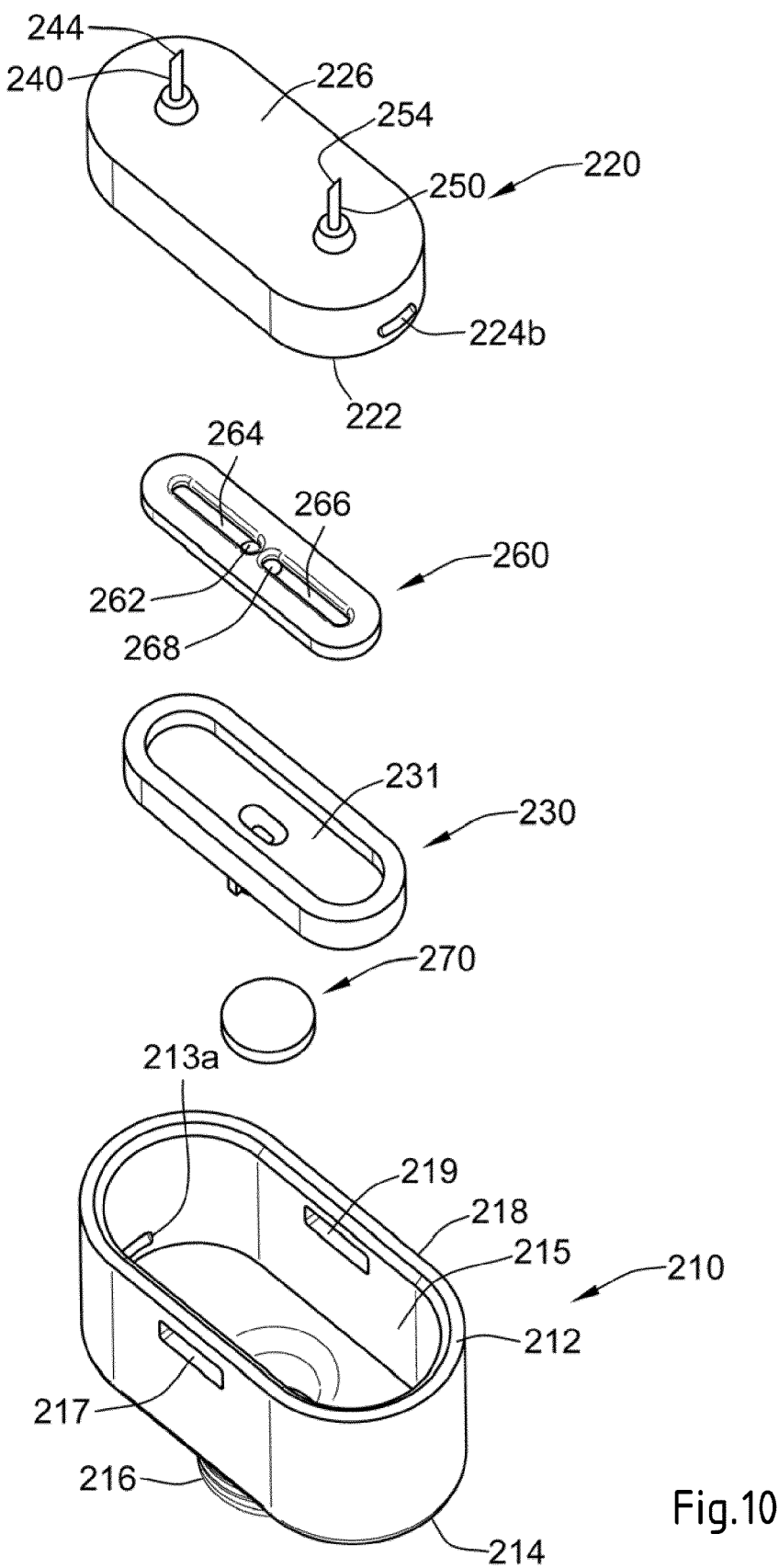
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber

280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet of the interface 200. This outlet 290 is preferably centrally located in the needle hub 216 of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
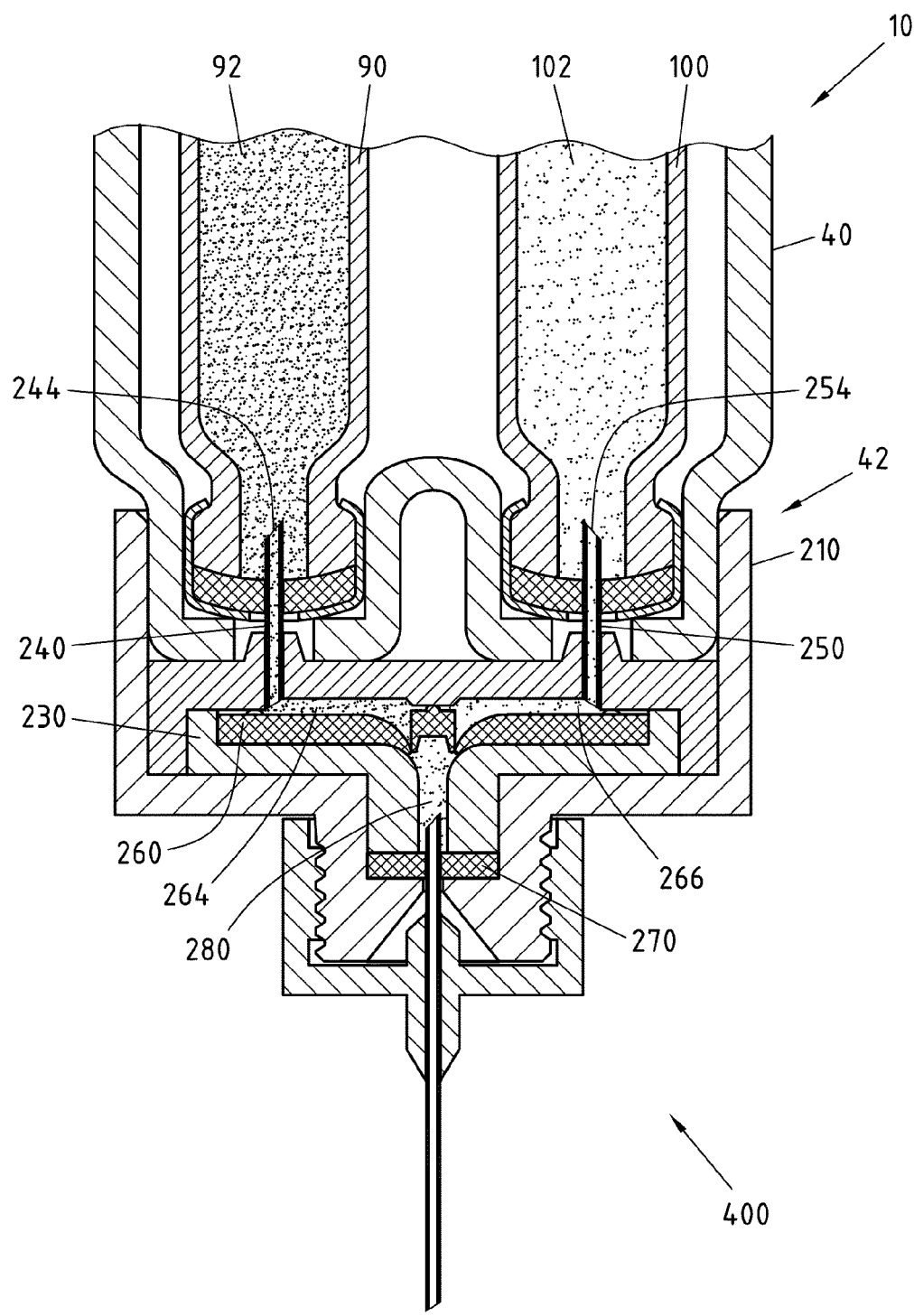
FIG. 11 illustrates a cross-sectional view of the dispense interface and dose dispenser attached to a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12A:
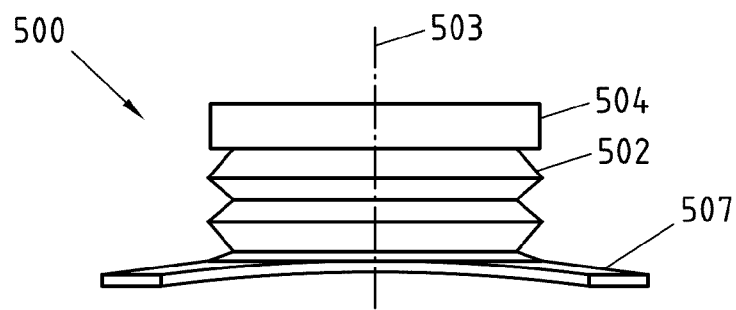
FIG. 12 illustrates an arrangement of a needle guide.
Figure 12B:
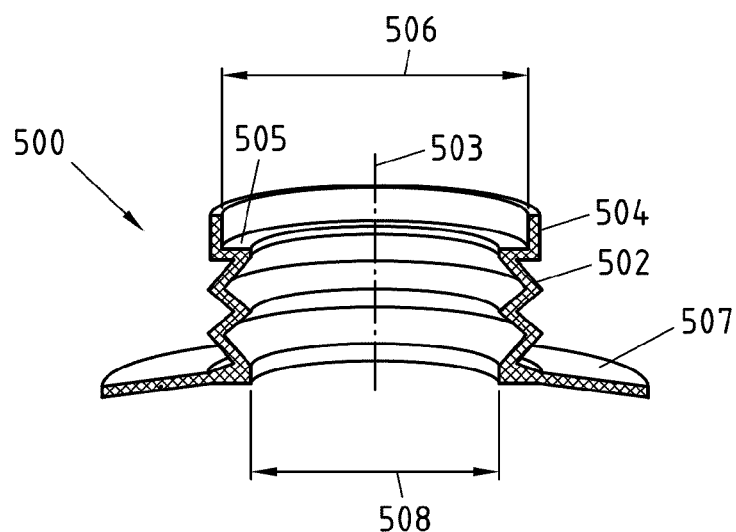
Figure 12C:
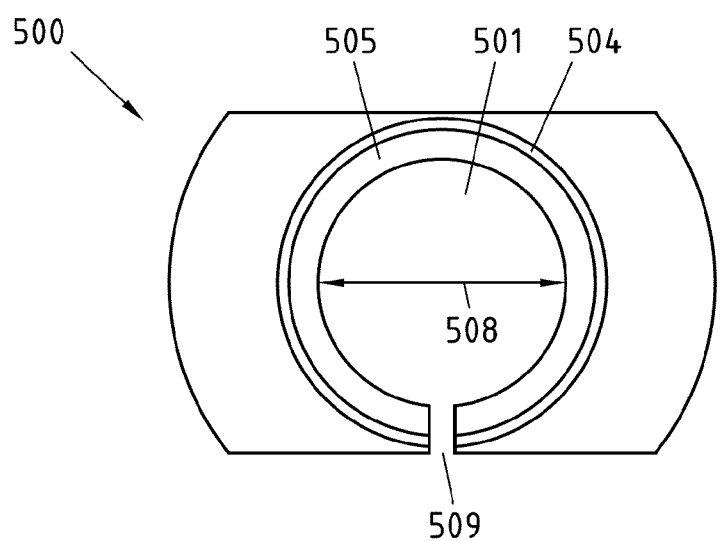

FIG. 12*a* to *c* illustrate an arrangement of a needle guide 500. The needle guide 500 has a longitudinal through opening 501. The opening 501 has a round cross section and is defined by a foldable lateral surface 502. The foldable lateral surface 502 is in direction of the longitudinal axis 503 of the opening 501 bellows like and has a longitudinal cross section comprising two sequentially arranged "V-shaped" portions. The foldable lateral surface 502 allows a reversible compression of the opening 502 in direction of the axis 503.

A rim 504 is arranged at one end of the opening 501 and a setback 505 is arranged at the rim 504. At the setback 505 the opening 501 has an inner diameter 506. The inner diameter 506 corresponds (e.g. is equal to or less than or, alternatively, equal to or not less than) to the outer diameter 422 at the rim 421 of the needle assembly 400 illustrated in FIG. 4. At the other end of the opening 501, a basis 507 is arranged. At the basis 507 the opening 501 has an inner diameter 508. The inner diameter 508 corresponds (e.g. is equal to or less than) to the outer diameter at the end 219 of the needle hub 216 of the dispense interface 200 illustrated in FIG. 4.

The needle guide 500 is made from an elastic material such as elastic plastics and the opening 501 has a longitudinal slit 509 which allows to spread the opening 501 and to enlarge the inner diameters (e.g. diameters 506, 508) of the opening 501.

Figure 13:
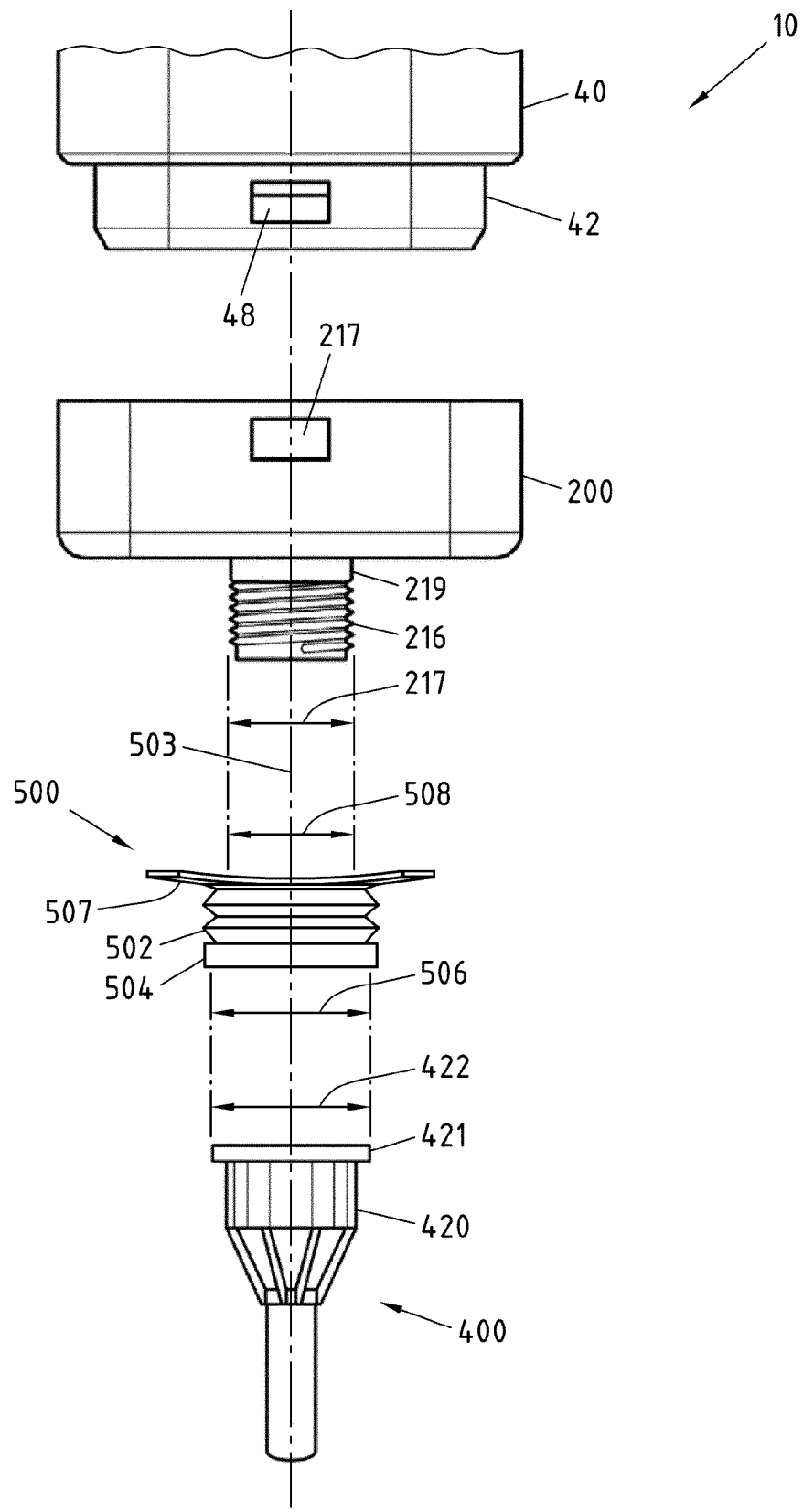
FIG. 13 illustrates a dispense interface that may be removably mounted on a distal end of the delivery device illustrated in FIG. 1 and a needle assembly that may be removably mounted on the dispense interface by use of a needle guide.

FIG. 13 illustrates the dispense interface 200 illustrated in FIGS. 7 to 10 that may be removably attached to the distal end 42 of the delivery device 10 illustrated in FIG. 1 and the needle assembly 400 illustrated in FIG. 6 that may be removably attached on the dispense interface 200 by use of the needle guide 500 illustrated in FIG. 12.

As illustrated in FIG. 13 the needle guide 500 is arranged between the needle assembly 400 and the dispense interface 200. Therein, base 507 of the needle guide 500 is oriented towards the dispense interface 200 and the rim 504 of the needle guide 500 is oriented towards the needle assembly 400 and, additionally, the longitudinal axis 503 of the needle guide 500 is also the longitudinal axis of the drug delivery device 10, the dispense interface 200 and the needle assembly 400.

The inner diameter 508 at the base 507 of the needle guide 500 is equal to or less than the outer diameter 217 at the end 219 of the needle hub 216 of the dispense interface 200. Furthermore, the inner diameter 506 at the setback 505 (not shown) of the needle guide 500 is equal to or less than the outer diameter 422 at the rim 421 of the needle assembly 400.

The needle assembly 400 may be attached to the dispense interface 200 by use of the needle guide 500 as follows.

Figure 14:
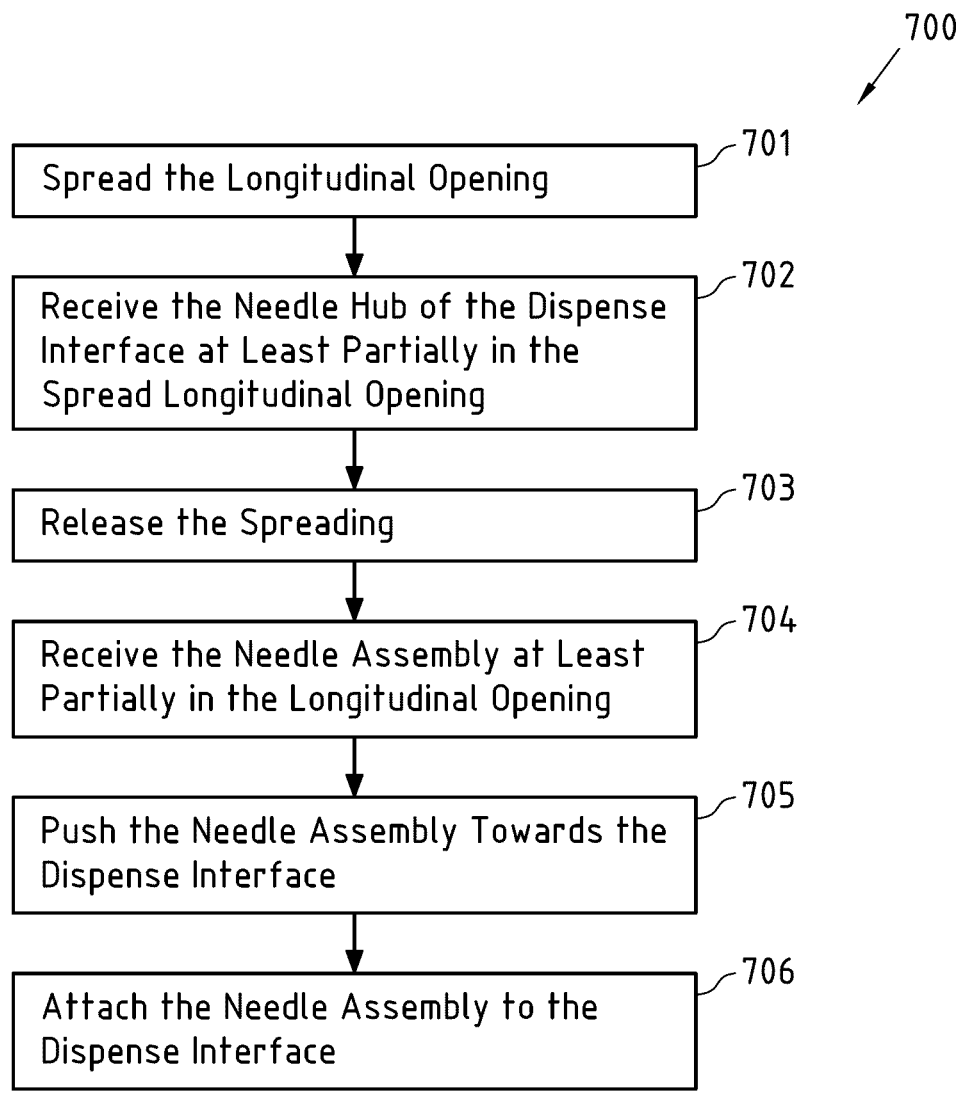
FIG. 14 illustrates a method for attaching a needle assembly to a dispense interface by use of a needle guide.

FIG. 14 illustrates a method 700 for attaching the needle assembly 400 to the dispense interface 200 by use of the needle guide 500.

In a step 701, the opening 501 of the needle guide 500 is spread by spreading the slit 509 of the opening 501 and thereby the inner diameters of the opening 501 are enlarged. In particular, the inner diameter 508 of the spread opening 501 is enlarged.

In a step 702, the needle hub 216 of the dispense interface 200 is received in the spread opening 501; and, in a step 703, the spreading is released. After releasing the spread, the opening 501 returns to its natural shape such that the inner diameter 508 of the spread opening 501 is equal to or less than the outer diameter 217 at the end 219 of the needle hub 216. Accordingly, the needle guide 500 is attached to the dispense interface 200 by forming a press fit or form fit connection with the end 219 of the of the needle hub 216 such that the opening 501 encompasses the needle hub 216 of the dispense interface 200 and the outlet 290 of the needle hub 216 is in the center of a cross section of the opening 501. Alternatively or additionally, the base 507 of the needle guide may be bonded (e.g. glued) to the surface of the dispense interface.

In a step 704, the needle assembly 400 is at least partially received in the opening 501. After at least partially receiving the needle assembly 400 in the opening 501, the rim 421 of the protective cover 420 resides on the setback 505 of the opening 501 and is laterally secured by the rim 504 of the opening 501 such that the double-ended needle 406 of the needle assembly 400 is centered in the opening. In particular, the piercing end 407 of the double-ended needle 406 is spaced from and centered on the outlet 290 of the needle hub 216. For instance, the needle assembly 400 at least partially forms a form fit connection with the opening 501.

In a step 705, the needle assembly 400 is pushed towards the dispense interface 200 along the longitudinal axis 503. Since the rim 421 of the protective cap 420 of the needle assembly resides on the setback 505 of the opening 501, the rim 504 of the opening 501 is also pushed towards the dispense interface 200 along the longitudinal axis 503 such that the lateral surface 502 of the opening 501 is folded and the opening 501 is compressed. Therein, the rim 421 of the protective cap 420 of the needle assembly remains on the setback 505 and is laterally secured by the rim 504 of the opening 501 such that the piercing end 407 of the double-ended needle 406 straightly approaches the outlet 290 along the axis 503.

When the needle hub 401 of the needle assembly 400 touches the needle hub 216 of the dispense interface, in a step 706, the needle assembly 400 is attached to the dispense interface 200.

Therein, the rim 421 of the protective cap 420 of the needle assembly still remains on the setback 505 and is laterally secured by the rim 504 of the opening 501. As described above, the internal thread 404 of the needle hub 401 of the needle assembly is screwed on the outer thread 218 of the needle hub 216 of the dispense interface 200 and thereby the piercing end 407 of the double-ended needle 406 intrudes into the outlet 290 of the needle hub 216, pierces the septum 270 arranged at the outlet 290 and resides in fluid communication with the holding chamber 280 of the dispense interface 200. The holding chamber may be in fluid communication with the first and second proximal needle.

Accordingly, the risk of a collision of the double-ended needle 406 with side-walls of the holding chamber 280 is significantly reduced, such that the cross-sectional inner diameter of the holding-chamber 280 may correspond to the outer diameter of the double ended needle 406.

Alternatively, the needle assembly 400 may firstly be received in the opening 501 of the needle guide 500 and, thereafter, the needle guide 500 may be attached to the dispense interface 200. For instance, firstly the steps 704 to 706 and, thereafter, the steps 701-703 may be performed.

Figure 15:
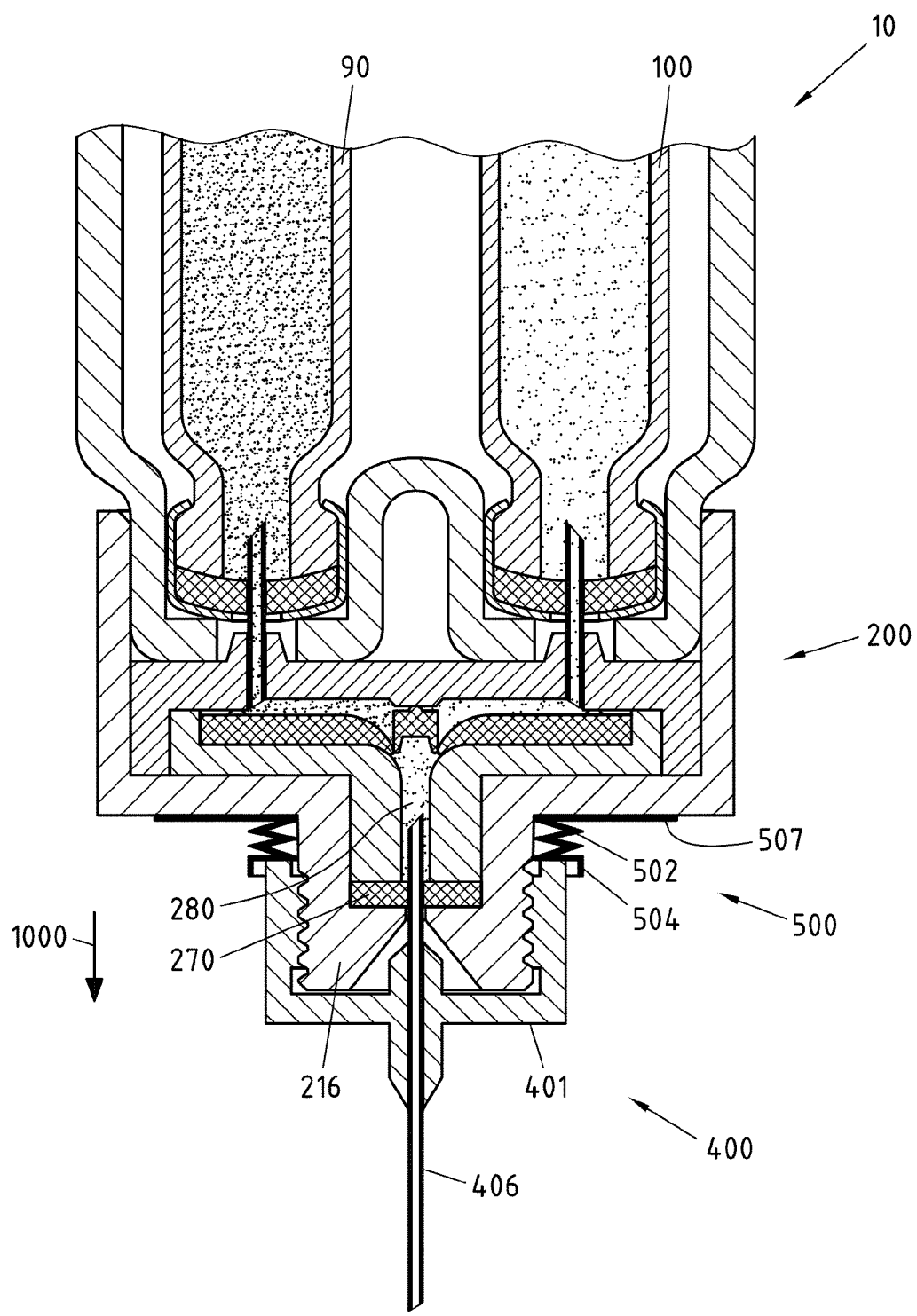
FIG. 15 illustrates a cross-sectional view of the dispense interface, needle guide and dose dispenser attached to a drug delivery device, such as the device illustrated in FIG. 1.

FIG. 15 illustrates a cross-sectional view of the dispense interface 200 illustrated in FIGS. 7-10, needle guide 500 illustrated in FIG. 12 and needle assembly 400 illustrated in FIG. 6 attached to a drug delivery device 10 illustrated in FIG. 1. At this point, it is mainly referred to the above description of the arrangement illustrated in FIG. 11 and, basically, the differences are described only.

As illustrated in FIG. 15, the needle hub 401 of the needle assembly 400 is screwed onto the needle hub 216 of the dispense interface 200. Therein, the sleeve 403 of the needle hub 401 resides on the setback 505 of the needle guide 500 and longitudinally compresses the opening 501 such that the lateral surface 502 of the longitudinal opening is folded. In response to the compression, an elastic counterforce in the direction of arrow 1000 is caused by the lateral surface 502. This counterforce may secure the screw connection between the dispense interface 200 and the needle assembly 400.

The present invention is inter-alia advantageous in order to facilitate attaching needle assembly 400 to the needle hub 216 of the dispense interface 200. Furthermore, the present invention is inter-alia advantageous in order to minimize the liquid dead volume in the dispense interface and/or in front of the cartridges 90 and 100 of the drug delivery device 10 and to secure the screw connection between the dispense interface 200 and the needle assembly 400.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. An apparatus comprising:
a needle guide configured to at last partially receive a needle of a needle assembly in a longitudinal opening and to center said needle of said needle assembly in said longitudinal opening, wherein said needle guide is longitudinally compressible, wherein the longitudinal opening is defined by a longitudinally compressible lateral surface, and wherein the lateral surface has at least one longitudinal slit.

2. The apparatus according to claim 1, wherein said longitudinal opening has a circular cross-section and/or is cylindrical.

3. The apparatus according to claim 1, wherein said lateral surface is foldable.

4. The apparatus according to claim 3, wherein said foldable lateral surface is formed like bellows.

5. The apparatus according to claim 1, wherein said lateral surface is made from an elastic material.

6. The apparatus according to claim 1, wherein said longitudinal opening has a circular set-back configured to receive a rim of said needle assembly.

7. The apparatus according to claim 1, wherein said needle guide is configured to encompass a connecting part of a medical device.

8. The apparatus according to claim 7, wherein said apparatus is attachable to said medical device.

9. The apparatus according to claim 1, wherein said apparatus is a medical device configured to eject a medicament, and wherein said needle guide encompasses a connecting part of said medical device.

10. The apparatus according to claim 7, wherein a needle hub of said needle assembly is configured to be attached to said connecting part of said medical device.

11. The apparatus according to claim 10, wherein one end of a needle of said needle assembly is configured to intrude into an outlet of said connecting part and to pierce a septum of said medical device.

12. The apparatus according to claim 1, wherein the longitudinal opening has a first end and a second end, and wherein the needle guide comprises a rim at one end of the longitudinal opening and a base at the other end of the longitudinal opening.

13. The apparatus according to claim 12, further comprising a setback arranged in the rim.

14. The apparatus according to claim 12, wherein said lateral surface is foldable.

15. The apparatus according to claim 8, wherein the medical device comprises a needle assembly and a dispense interface, and wherein the needle guide is arranged between the needle assembly and a dispense interface.

16. The apparatus according to claim 15, wherein the needle guide is configured to be attachable to the dispense interface by a press fit or form fit connection.

17. The apparatus according to claim 15, wherein the needle guide is configured to be bonded to the dispense interface.

18. A method comprising:
receiving, at an apparatus, a needle of a needle assembly in a longitudinal opening of a needle guide, and
centering said needle of said needle assembly in said longitudinal opening, wherein said needle guide is longitudinally compressible and wherein said needle guide includes at least one longitudinal slit.

19. The method according to claim 18, said method comprising:
longitudinally compressing said needle guide,
attaching said needle assembly to a connecting part of a medical device,
intruding said needle of said needle assembly into an outlet of said connecting part, and
piercing a septum of said medical device.

* * * * *